United States Patent [19]

Tinman

[11] 4,282,655
[45] Aug. 11, 1981

[54] CARDIAC AXIS CALCULATOR

[76] Inventor: Daniel Tinman, 2656 Hampshire Rd., Cleveland Heights, Ohio 44106

[21] Appl. No.: 111,243

[22] Filed: Jan. 11, 1980

[51] Int. Cl.³ .............................................. G01B 3/00
[52] U.S. Cl. ..................................... 33/1 C; 33/465; 33/472
[58] Field of Search .............. 33/1 C, 15 D, 403, 418, 33/419, 456, 457, 425, 464, 472, 1 N, 431, 465, 468

[56] References Cited

U.S. PATENT DOCUMENTS

| | | | |
|---|---|---|---|
| 1,691,279 | 11/1928 | Gates | 33/472 |
| 2,419,203 | 4/1947 | Edwards | 33/457 |
| 3,238,625 | 3/1966 | Myers | 33/472 |
| 3,621,578 | 9/1969 | Novakovic | 33/457 |
| 3,766,652 | 10/1973 | Gomez | 33/472 |
| 4,030,486 | 6/1977 | Eastman | 33/1 C |

Primary Examiner—William D. Martin, Jr.
Attorney, Agent, or Firm—Duffield & Lehrer

[57] ABSTRACT

A device for determining the mean cardiac axis for aiding in the interpretation of an electrocardiograph includes a disc shaped member having a pair of radially extending arms pivotally attached to the center of the disc. The disc also carries a plurality of radial line markings thereon and preferably spaced every fifteen degrees. At least two of the radial markings, the one at 0° and the one at 120° representing the first and third EKG leads, have millimeter graduations thereon. Each arm has an elongated slide thereon which when positioned at the proper magnitude setting along the proper radial marking intersects the other slide to indicate the cardiac axis.

6 Claims, 3 Drawing Figures

CARDIAC AXIS CALCULATOR

BACKGROUND OF THE INVENTION

This invention relates to a cardiac axis calculator and more particularly toward a hand manipulative device which can quickly and easily determine the mean cardiac axis by reference to and for use with an electrocariograph.

As is well known in the medical field, an electrocardiograph, commonly referred to as an EKG, reveals very valuable information relating to the operation and condition of the human heart. The EKG assumes, however, that the heart is properly positioned in the chest cavity. It is not uncommon for the heart to be tilted to one direction or the other and still function properly. The EKG reading is affected by the position of the heart and accordingly in order to properly interpret the EKG, the position of the heart must first be determined.

Heretofore, a very experienced cardiologist could examine an EKG and within a reasonable degree of accuracy could ascertain the mean cardiac axis, sometimes referred to as the main QRS vector. However, this cannot always be done by a mere visual examination of the EKG and some less experienced medical personnel are not able to readily ascertain the vector. There is, therefore, believed to be a need for a simple and inexpensive device which is capable of quickly and easily determining the QRS vector.

SUMMARY OF THE INVENTION

The present invention is believed to satisfy the need referred to above and is directed toward a device which is capable of quickly and easily determining the mean cardiac axis. The device of the present invention includes a disc shaped member having a pair of radially extending arms pivotally attached to the center of the disc. The disc also carries a plurality of radial line markings thereon and preferably spaced every fifteen degrees. At least two of the radial markings, the one at 0° and the one at 120° representing the first and third EKG leads, have millimeter graduations thereon. Each arm has an elongated slide thereon which when positioned at the proper magnitude setting along the proper radial marking intersects the other slide to indicate the cardiac axis.

BRIEF DESCRIPTION OF THE DRAWINGS

For the purpose of illustrating the invention, there is shown in the accompanying drawing one form which is presently preferred; it being understood that the invention is not intended to be limited to the precise arrangements and instrumentalities shown.

DETAILED DESCRIPTION OF THE PREFERRED EMBODIMENT

Figure 1:
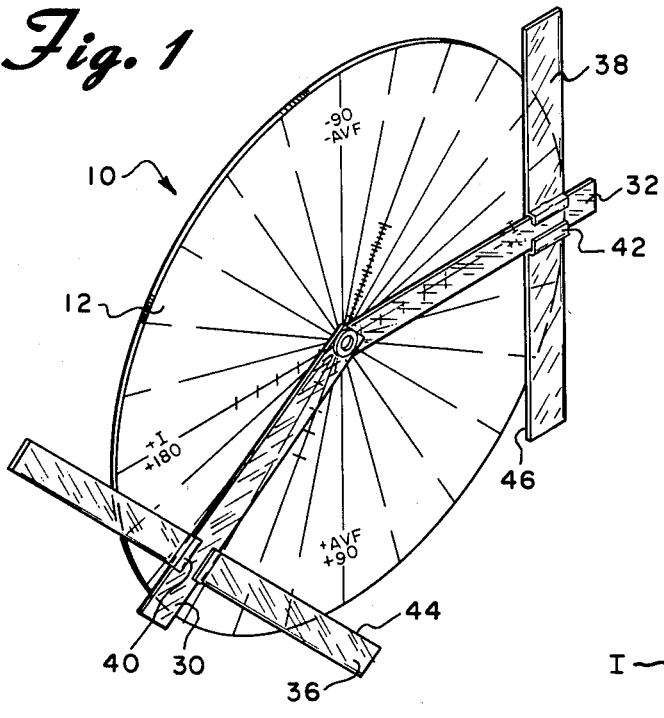
FIG. 1 is a perspective view of a cardiac axis calculator constructed in accordance with the principles of the present invention.

Referring now to the drawings in detail wherein like reference numerals have been used throughout the various figures to designate like elements, there is shown in FIG. 1 a perspective view of a cardiac axis calculator constructed in accordance with the principles of the present invention and designated generally as 10. Calculator 10 includes a base in the form of a planar circular disc shaped member 12. While the size of the disc 12 is not critical, it has been found that a circular disc having a diameter of approximately six inches is preferable.

Figure 2:
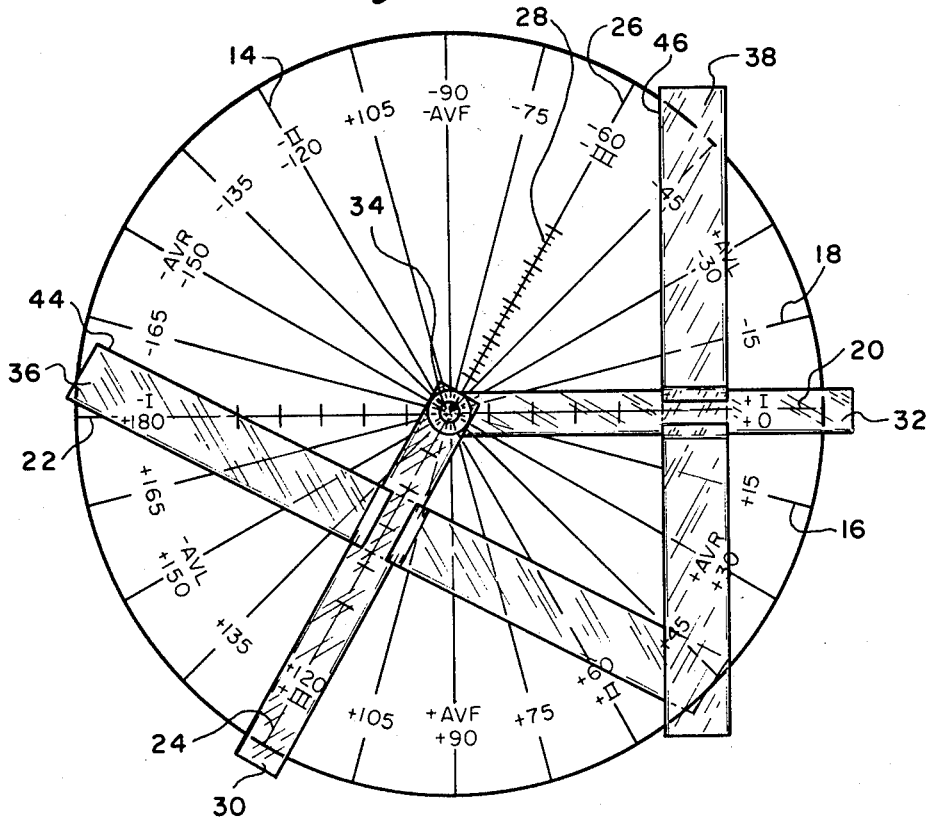
FIG. 2 is a front plan view thereof showing the details of the markings on the device.

As shown most clearly in FIG. 2, the disc 12 has a plurality of radial lines 14 thereon which extend from the center point of the circle to the periphery of the disc. The radial lines 14 may be printed, engraved or otherwise formed on the disc 12. Preferably, there are twenty-four equally spaced radial lines 14 at 15° intervals.

For the reasons which will become more apparent hereinafter, each of the radial lines 14 is identified by its angular value. In addition, the lines on one-half of the disc 12 are identified as positive angles and the lines on the other half of the disc are indicated to be negative angles. For example, line 16 is identified as +15° and line 18 in the other half of the disc is labeled as −15°. Furthermore, the 0° radial line 20 and the 180° radial line 22 have the notations +I and −I, respectively, noted thereon which indicates that these lines correspond to the first electrode of the EKG. Similarly, lines 24 and 26 have the notations +III and −III, respectively, indicating that these lines correspond to the third EKG electrode.

While the radial lines corresponding to the first and third electrodes are described above, it should be understood that other radial lines corresponding to other electrodes could also be utilized. It has been found, however, that adequate results are obtained utilizing the first and third electrodes only. Each of the radial lines which have been idenified by the notation +I, −I, −III or −III also have thereon a scale such as shown at 28 and which is preferably marked in millimeters.

A pair of radially extending arms 30 and 32 are pivotally attached to the center of the disc 12 by a rivet or similar fastening device 34 which passes through the arms 30 and 32 and the disc 12. The arms 30 and 32 are capable of rotating about the surface of the disc 12 around the center point 34. Preferably, the arms 30 and 32 are composed of a transparent material so that the markings on the disc 12 there below can be seen through the arms.

Slideably attached to arm 30 is an elongated slide 36 and similarly attached to arm 32 is an elongated slide 38. As shown most clearly in FIG. 1, the slides 36 and 38 are attached to the arms 30 and 32 by way of slideable connectors 40 and 42 secured to the slides in which engage the arms. Slides 36 and 38 are also preferably made of a transparent material so that the markings on the disc 12 may be seen there through. In addition, each slide includes an elongated element thereon such as the leading edges 44 and 46 which are substantially perpendicular to the respective arms 30 and 32. Alternatively, a straight line may be drawn or etched or otherwise formed on the transparent slides 36 and 38 so as to be perpendicular to the respective arm.

The device of the present invention is utilized in the following manner. First, one examines the EKG and particularly the graph corresponding to lead 1 thereof. This is shown in the upper part of FIG. 3. The height of the "R" wave is first measured in millimeters and the height of the "S" wave also measured in millimeters is subtracted from the value of the R wave. If the result is positive, i.e. R was greater than S, arm 32 is positioned on the +I radial line. If, on the other hand, the result was negative, i.e. S was greater than R then the arm 32 would be positioned over the −I radial line. In the examples shown in FIG. 3, the height of the R wave exceeds the negative deflection of the S wave by +5 millimeters. Accordingly, as shown in FIG. 2, the arm 32 is positioned along the −I radial line and the slide 38 is adjusted such that the leading edge element 46 is five millimeters from the center point 34.

Figure 3:
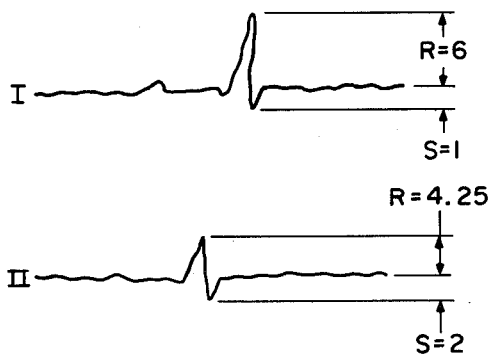
FIG. 3 is a graphical representation of a partial EKG which will be used to demonstrate the operation of the invention.

The graph corresponding to the third leads shown in the lower portion of FIG. 3 is then examined. It can there be seen that the height of the "R" wave exceeds the negative deflection of the "S" wave by approximately 2.25 millimeters. Accordingly, the arm 30 is lined with the +III radial line 24 and the slide 36 is adjusted so that the forward edge 44 is at approximately 2.25 millimeters. As can be seen in FIG. 2, the leading straight edge 44 of the slide 36 and the leading edge 46 of the slide 38 intersect at the +45° radial line. Thus, the main QRS vector, i.e. the mean cardiac axis is 45°.

The present invention may be embodied in other specific forms without departing from the spirit or essential attributes thereof and accordingly, reference should be made to the appended claims rather than to the foregoing specification as indicating the scope of the invention.

I claim:

1. A device for determining the mean cardiac axis in connection with an electrocardiograph comprising:
   a substantially planar disc shaped member having a plurality of radial lines thereon;
   a pair of radially extending arms pivotally attached to a point on said disc shaped member, and
   a pair of elongated slides, each slide being carried by a different one of said arms and being adapted to slide radially along the length of the arm, each slide including an elongated element thereon which is substantially perpendicular to its respective arm.

2. The device as claimed in claim 1 wherein said disc is circular.

3. The device as claimed in claim 2 wherein said arms are pivotally attached to said disc substantially at the center thereof.

4. The device as claimed in claim 1 wherein at least two of said radial lines have graduated markings thereon.

5. The device as claimed in claim 1 wherein said elongated element is comprised of an edge of said slide.

6. The device as claimed in claim 1 wherein each of said slides is substantially transparent.

* * * * *